United States Patent
Li et al.

(10) Patent No.: US 11,013,462 B2
(45) Date of Patent: May 25, 2021

(54) ELECTROCARDIOGRAM SENSOR RING

(71) Applicant: The George Washington University, Washington, DC (US)

(72) Inventors: Zhenyu Li, McLean, VA (US); Quan Dong, Arlington, VA (US); Mona Zaghloul, Bethesda, MD (US)

(73) Assignee: The George Washington University, Washington, DC (US)

( * ) Notice: Subject to any disclaimer, the term of this patent is extended or adjusted under 35 U.S.C. 154(b) by 325 days.

(21) Appl. No.: 15/547,931

(22) PCT Filed: Feb. 18, 2016

(86) PCT No.: PCT/US2016/018510
§ 371 (c)(1),
(2) Date: Aug. 1, 2017

(87) PCT Pub. No.: WO2016/134170
PCT Pub. Date: Aug. 25, 2016

(65) Prior Publication Data
US 2018/0020977 A1   Jan. 25, 2018

Related U.S. Application Data

(60) Provisional application No. 62/117,679, filed on Feb. 18, 2015.

(51) Int. Cl.
*A61B 5/00* (2006.01)
*A61B 5/30* (2021.01)
(Continued)

(52) U.S. Cl.
CPC ............ *A61B 5/6802* (2013.01); *A61B 5/002* (2013.01); *A61B 5/282* (2021.01); *A61B 5/30* (2021.01);
(Continued)

(58) Field of Classification Search
CPC ..... A61B 5/6802; A61B 5/002; A61B 5/6826; A61B 5/0006; A61B 5/0245;
(Continued)

(56) References Cited

U.S. PATENT DOCUMENTS 5,365,935 A * 11/1994 Righter ............... A61B 5/0404
600/523
6,950,695 B2 * 9/2005 Chen .................. A61B 5/02438
600/509

(Continued)

FOREIGN PATENT DOCUMENTS

WO   WO-2014116816 A1   7/2014

OTHER PUBLICATIONS

Wang et al., "Wearable mobile electrocardiogram measurement device with novel dry polymer-based electrodes," TENCON 2010-2010 IEEE Region 10 Conference, IEEE, 2010. pp. 379-384. [retrieved on Apr. 14, 2016],Retrieved from the internet,URL:https://www.researchgate.net/profile/YU-Te_Wang/publication/241178839_A-Wearable_Mobile_Electrocardiogram_Measurement_Device_with_Novel_Dry_Polymer-based_Electrodes/links/54cac5880cf2c70ce523e520.pdf.; figure 3; secions iiB, IId, IIIA.

(Continued)

*Primary Examiner* — Linda C Dvorak
*Assistant Examiner* — Annabeth E Rodriguez
(74) *Attorney, Agent, or Firm* — Blank Rome LLP

(57) ABSTRACT

An electrocardiogram (ECG) sensor has a flexible thin ring-shaped substrate configured to be worn about a patient's finger. The substrate has an inner surface and an outer surface opposite the inner surface. A first ECG electrode is positioned at the outer surface of said substrate and a second ECG electrode is positioned at the inner (or outer) surface of the said substrate in contact with the finger (or the adjacent finger if the electrode is on the outer surface), (Continued)

whereby the two ECG electrodes receives a single-lead ECG signal when the first electrode is touched to the patient's body. Touching different locations on the body or wearing multiple rings can provide multi-lead ECG measurements. The ring shape can be converted to a wearable patch for continuous ECG measurements.

25 Claims, 12 Drawing Sheets

(51) Int. Cl.
    *A61B 5/282*     (2021.01)
    *A61B 5/332*     (2021.01)
    *H05K 1/02*     (2006.01)

(52) U.S. Cl.
    CPC ............ *A61B 5/332* (2021.01); *A61B 5/6826* (2013.01); *A61B 2562/125* (2013.01); *A61B 2562/166* (2013.01); *H05K 1/028* (2013.01)

(58) Field of Classification Search
    CPC ... A61B 5/0402; A61B 5/0423; A61B 5/0428; A61B 5/0468; A61B 5/318; A61B 5/322; A61B 5/364; H05K 1/028
    See application file for complete search history.

(56) References Cited

U.S. PATENT DOCUMENTS

| | | | |
|---|---|---|---|
| 2002/0026114 A1* | 2/2002 | Nissila | A61B 5/02438 600/384 |
| 2003/0100840 A1* | 5/2003 | Sugiura | A61B 5/0059 600/504 |
| 2007/0040258 A1 | 2/2007 | Sheats | |
| 2010/0127407 A1 | 5/2010 | LeBlanc et al. | |
| 2011/0066081 A1* | 3/2011 | Goto | A61B 5/1118 600/595 |
| 2012/0116176 A1* | 5/2012 | Moravec | A61B 5/6898 600/300 |
| 2014/0228665 A1* | 8/2014 | Albert | A61B 5/0022 600/384 |
| 2014/0375465 A1 | 12/2014 | Fenuccio et al. | |

OTHER PUBLICATIONS

Meyer et al., "Wearable silver nanowire dry electrodes for electrophysiological sensing," RSC Advances, 5(15), Jan. 14, 2015, pp. 11627-11632. [retrieved on Apr. 15, 2016]. Retrieved from the internet<URL:http://rec.bme.unc.edu/files/Huang%20Publications/Wearable_silver_nanowire_ dry_electrodes_for.pdf; p. 1167, 1st and 2nd paragraphs.
International Search Report and Written Opinion issued in PCT/US16/18510 dated May 6, 2017.

* cited by examiner

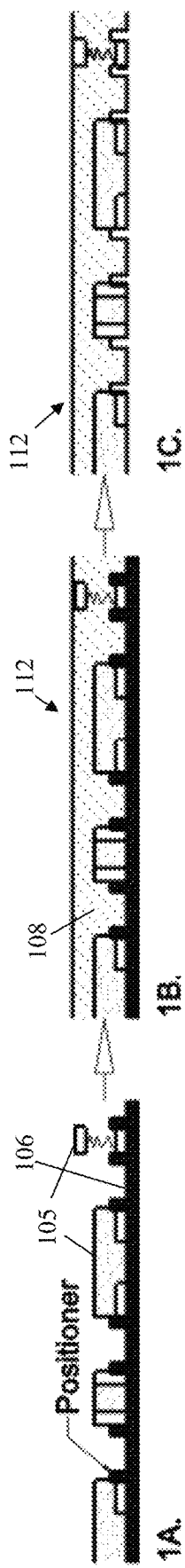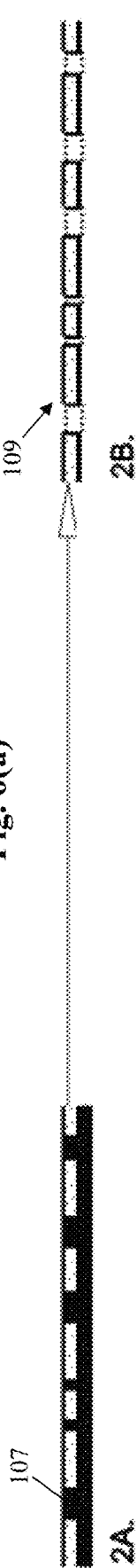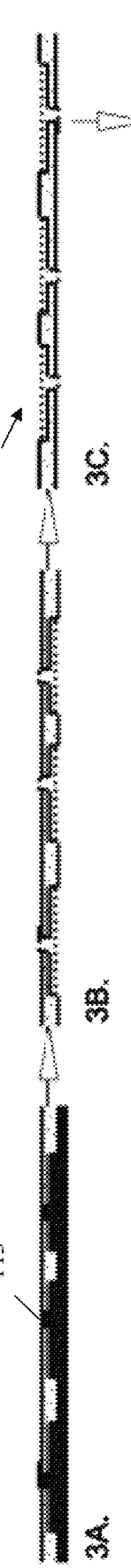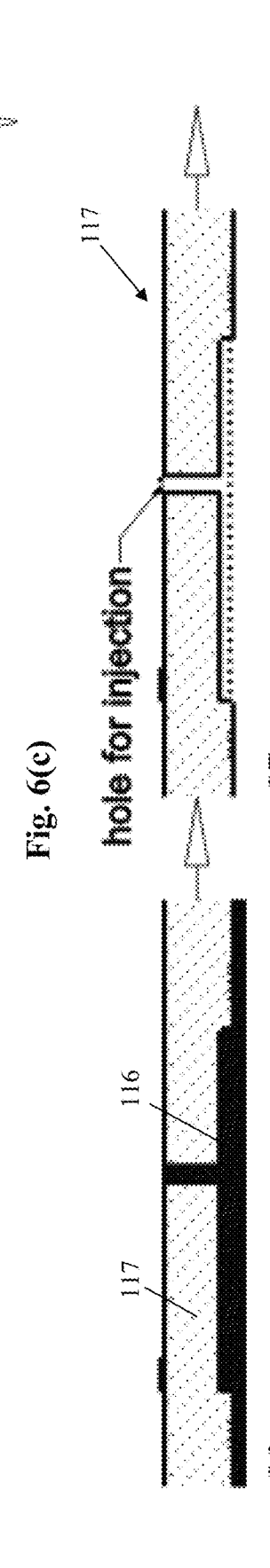
Fig. 6(a)
Fig. 6(b)
Fig. 6(c)
Fig. 6(e)

7.

8.

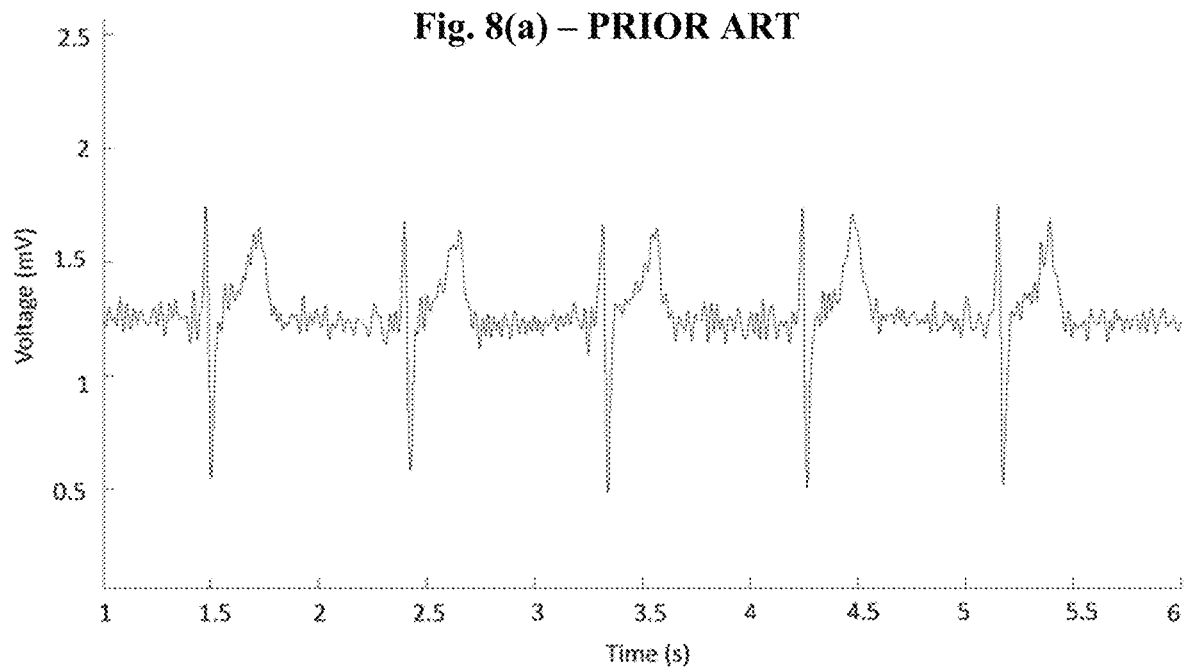
Fig. 8(a) – PRIOR ART
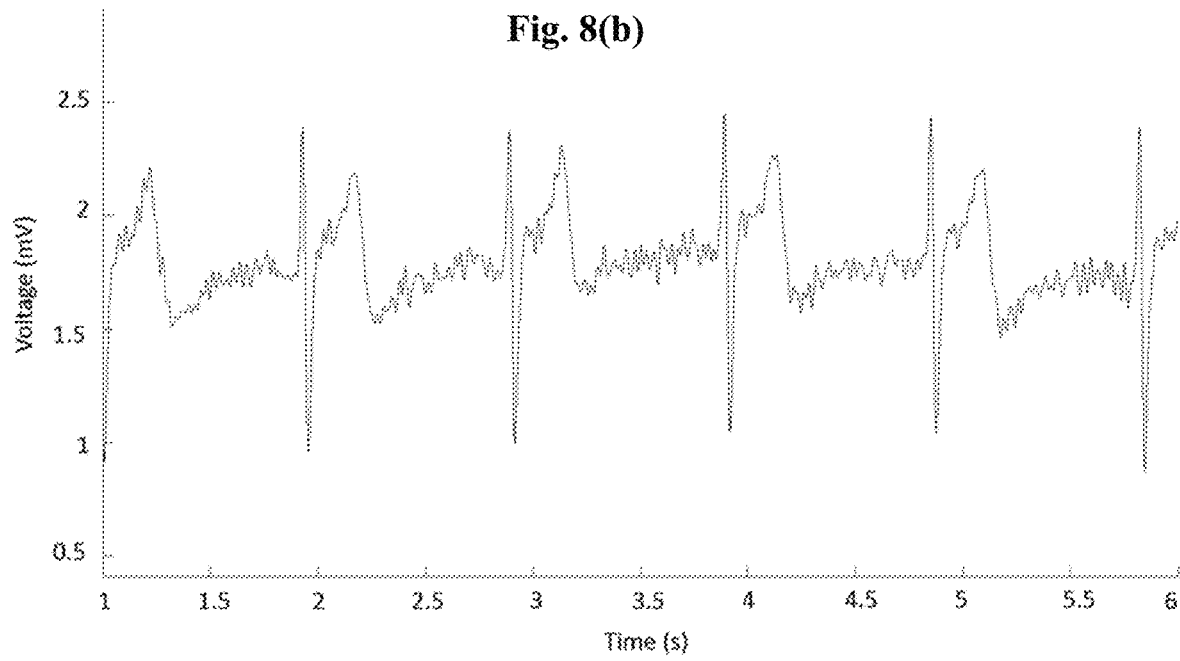
Fig. 8(b)

ELECTROCARDIOGRAM SENSOR RING

RELATED APPLICATION

This application is a national phase of PCT/US2016/018510, filed on Feb. 18, 2016, which claims the benefit of U.S. Provisional Application No. 62/117,679, filed Feb. 18, 2015. The entire contents of those applications are hereby incorporated herein by reference.

BACKGROUND OF THE INVENTION

Field of the Invention

The present invention relates to electrocardiogram (ECG) systems. More particularly, the present invention relates to a flexible ring having an ECG sensor.

BACKGROUND OF THE RELATED ART

An electrocardiogram (ECG) is an important tool widely used in the clinical diagnosis of heart diseases. It can be used to diagnose symptoms of myocardial infarction, pulmonary embolism, etc. [1] Among those symptoms, detection and early warning of the potential sudden cardiac events such as myocardial infarction can be crucial in daily life for patients, especially those who live alone, because it needs to be taken care of immediately. Every year over 380,000 Americans die from a heart attack, of which one third happens outside a hospital. A personalized cardiac monitoring device capable of on-demand diagnosis may help reduce this number and save lives. Unfortunately, the traditional equipment currently used in the hospital cannot fulfill this real-time on-demand monitoring requirement.

The important role ECG plays in heart disease diagnostic and the convenient noninvasive way of measurement makes it an ideal candidate to be converted to wearable healthcare devices, and have already drawn researchers' attention. For instance, Y. Chi and G. Cauwenberghs have demonstrated a wireless ECG/EEG monitoring system using noncontact electrodes. [2] The gel free noncontact electrodes make the wearing of the device more comfortable and cleaner. However, their electrodes are rigid which makes it less compatible to soft human bodies. Moreover, it is uncomfortable to wear several hard electrodes of noticeable sizes.

ALIVECOR® developed a single-lead ECG monitoring system in the smartphone case format, which can monitor the ECG at the fingertip and displays on the smartphone screen. This system has gotten FDA approval, which confirms the possibility to achieve a wearable ECG system. Unfortunately, single-lead ECG measurements, which apply to all existing systems, cannot be used to diagnose myocardial infarction. The phone case format makes it convenient to carry around, but limits it to a single-lead measurement only.

IMEC developed a long term multiple-lead ECG monitoring patch, which can be attached to the upper body and last as long as one month. The only drawback is the usage of conduction gel, which is commonly used in the traditional ECG. The sticky gel is difficult to keep clean and some patients can be allergic to the gel [3]. The IMEC system uses Bluetooth Low Energy (BLE) to transfer data, which is suited for wearable healthcare equipment because of the low energy consumption and sufficient transfer rate. However, a dedicated BLE data transfer base device in their device is not necessary, because there are many BLE enabled devices available now, such as smartphones and laptops. Using a smartphone to communicate with these wearable devices is convenient, because people carry smartphone around and the smartphone has the ability to further analyze the data, to transfer the data to the physicians, and/or to upload the data to a cloud for storage or analysis.

IRHYTHM® developed a single-lead ECG monitoring patch, which can be attached to the upper body and last for 14 days [5]. The drawback is the usage of conduction gel, which is difficult to keep clean and can cause allergy to some patients.

However, all above mentioned systems provide only single-lead ECG measurement, and thus cannot be used for heart attack diagnosis. At least 3 leads of ECG data are needed to make a conclusive diagnosis of heart attacks [6].

SUMMARY OF THE INVENTION

Accordingly, it is an object of the invention to provide an ECG measurement system. It is a further object of the invention to provide an ECG sensor that is easy to use. It is yet another object of the invention to provide an easy to use ECG sensor that can be used with 3 or more data leads.

A wearable ECG monitoring system is provided that is capable of providing on-demand multiple-lead ECG signals in the format of a flexible finger ring. By simply touching the ring to different positions on the body, multi-lead ECG can be obtained with a single ring asynchronously. If simultaneous multi-lead ECG signals are needed, the user can wear multiple ring sensors and touch them simultaneous on different body locations to acquire the signals. Such ring form factor is enabled by a novel soft electronics/microfluidics co-packaging technique [4] described in U.S. Pat. No. 9,116,145, which is herein incorporated by reference. The flexibility is one key advantage to achieve a comfortable device, and also provides certain durability during impact.

These and other objects of the invention, as well as many of the intended advantages thereof, will become more readily apparent when reference is made to the following description, taken in conjunction with the accompanying drawings.

BRIEF DESCRIPTION OF THE FIGURES

FIGS. 6(a)-(h) are a single flow diagram showing the manufacturing process of the ring configuration of FIG. 5(a);

FIG. 8(a) is an ECG waveform diagram from a conventional ECG sensor;

FIG. 8(b) is an ECG waveform diagram from an ECG ring sensor of the present invention.

DETAILED DESCRIPTION OF THE PREFERRED EMBODIMENTS

Figure 1:
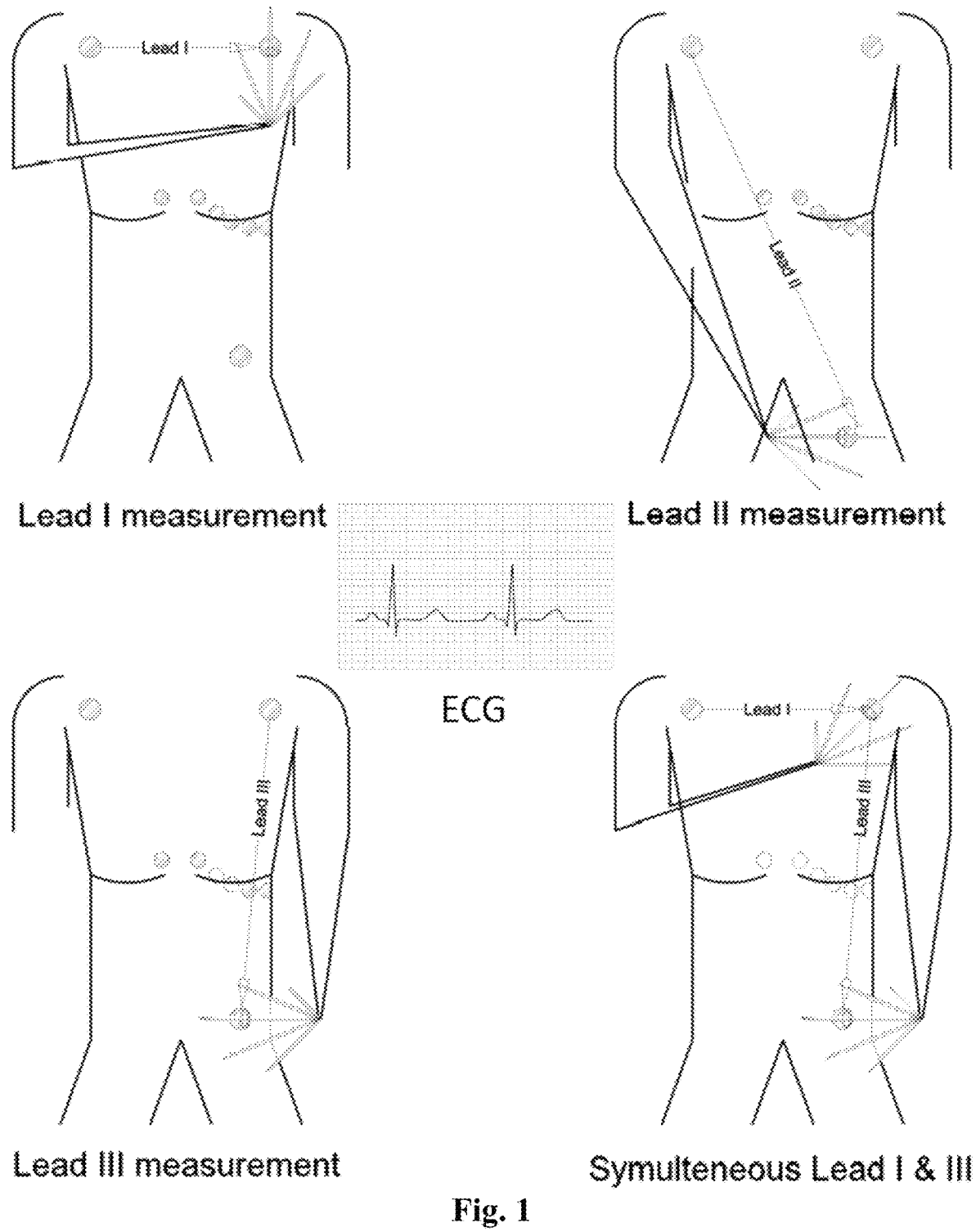
FIG. 1 shows the application of a finger ring sensor of the present invention for multi-lead ECG measurements.
Figure 2:
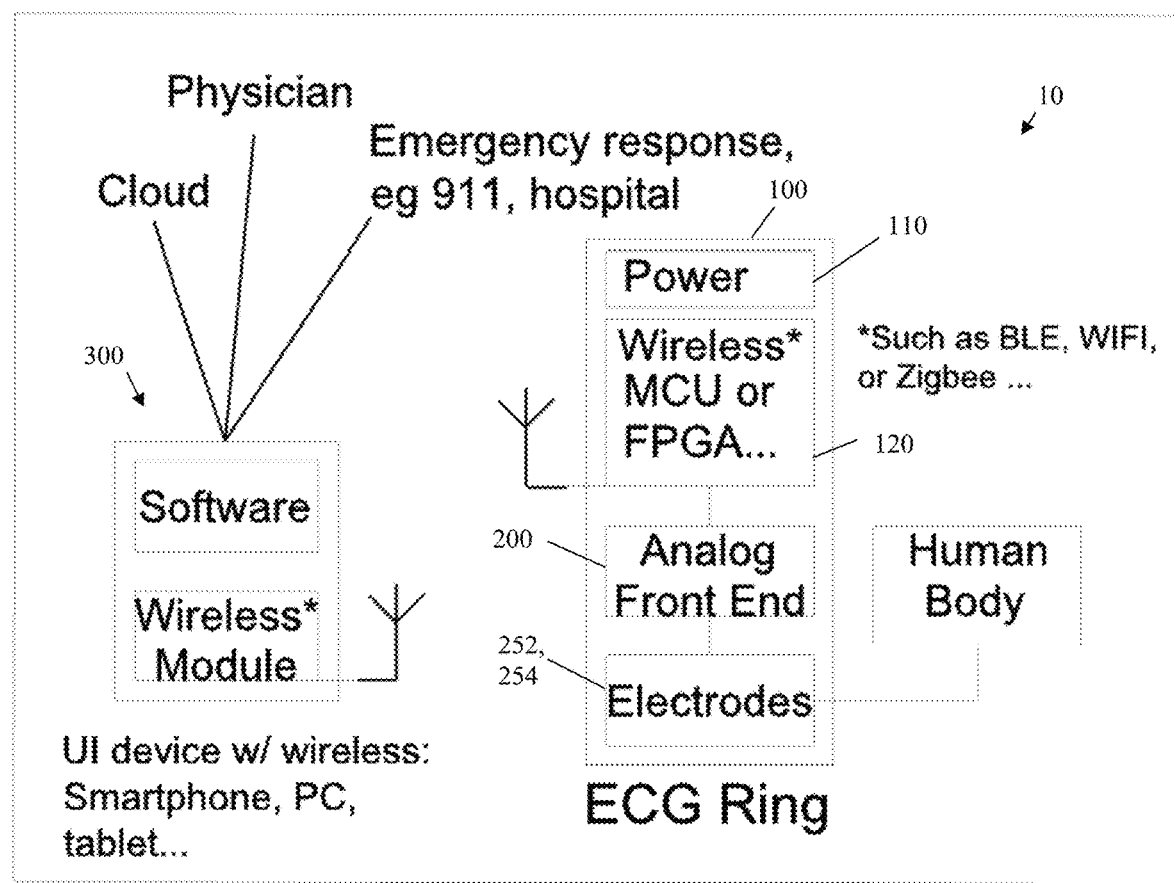
FIG. 2 is a system block diagram of the finger ring sensor system of the present invention.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents that operate in similar manner to accomplish a similar purpose. Several preferred embodiments of the invention are described for illustrative purposes, it being understood that the invention may be embodied in other forms not specifically shown in the drawings.

Turning to the drawings, the electrocardiogram (ECG) system 10 is shown in accordance with the invention. The system 10 includes a ring shaped ECG sensor 100 and a patient user input (UI) device (such as a smartphone, tablet, PC) 300. The ECG sensor 100 can be implemented as a ring or ring sensor that can have four components: power system 110, microcontroller system 120, analog front end 200, and electrodes 252, 254. The ring sensor 100 and the patient device 300 can each have a wireless module and associated software so that the ring sensor 100 can wirelessly communicate with the patient device 300. Thus, the patient device 300 can be separate (i.e., remote) from the sensor 100, though in close enough proximity to receive signals from the sensor 100.

The ring sensor 100 can be powered by button battery 110. Most of the time, the ring 100 can be in sleep mode to conserve the power. It can be woken up by the user by simple touch to conduct on-demand measurement, or it can wake up spontaneously by internal timer to perform scheduled measurement. The ECG measurement acquired in both these cases can be either stored in the on-chip flash memory device (which can be located at or in communication with the MCU 120) or transmitted by the ring 100 or the patient's device 300 to a medical practitioner such as a physician having a Bluetooth smart enabled device, such as a smartphone or a PC with Bluetooth smart peripherals. While doing real-time transmission, an ECG graph can be displayed in real time (as the ECG is taken, without delay) to the user at the patient's device 300.

To perform the measurement, the user wears the ring 100 on one hand, which causes a first electrode 252 inside the ring 100 to contact the user's wearing hand. By touching a second electrode 254 on the outside of the ring 100 to the opposite hand or the other parts of body other than the wearing limb, the user can obtain multi-lead ECG signals asynchronously, such as shown in FIG. 1. By wearing multi-rings 100, for example, one ring on each hand, the user is able to obtain multi-lead ECG signal synchronously. Or, the measurements can be taken at different times. Certain measurements may need to be taken at the same time. For instance, when simultaneous measurements are required, the chest and thigh need to be touched at the same time. Some of the dots shown in FIG. 1 represent a measurement taken at the patient's finger. For instance, in the Lead I measurement, the dot on the upper left (the right chest) represents the measurement taken by the electrode on the user's finger.

In addition, the ring 100 can be unwrapped into a patch and attached to a certain position of the body. In this case, the device 100 can be used to conduct continuous monitoring in addition to the on-demand and scheduled measurements which are also provided in the ring shape.

After the ECG data is acquired, pattern recognition technology can be applied by the microcontroller 120 to perform initial diagnosis in order to give the user some feedback and/or advice. By utilizing the wireless communication capability of these smart devices, the data and initial diagnosis can be sent to user's physician device 300 for professional diagnosis and record purposes. In this way, the device not only satisfies the need of the user for health monitoring, but also helps the physician with patient monitoring and quick diagnosis. Moreover, in some extreme conditions, like a heart attack, the software can contact emergency services automatically via preset method, like calling 911 using pre-recorded message. The ring sensor can also send its data to a cloud-based automated diagnosis center. The ring can also be connected to some intervention devices, such as drug delivery system, to form a close-loop system, to precisely and automatically maintain the health of the user.

The Microcontroller System 120

In a non-limiting illustrative embodiment of the invention, the microcontroller system 120 controls the operation of the whole system, including data acquisition, communication, and power management. Most of the time, the microcontroller system 120 is in sleep mode to conserve battery power. It is connected to a touch button through an interruption enabled pin. A simple touch will wake up the controller 120. By tapping the button with a predefined sequence, the user can initiate a measurement to be taken and save it in the on-chip flash memory. With another predefined tapping sequence, the user can also pair the ring with a smartphone 300 to conduct more sophisticated operation, like uploading previous measurement or viewing real-time ECG. The microcontroller 120 can also wake up spontaneously at scheduled time and inform the user to conduct a routine measurement, based on the configuration set during pairing with the smartphone.

The ring has some on-board program (e.g. microcontroller program) in order to save power, and can also pair with the smartphone 300 to perform more sophisticated tasks, including modifying settings used without smartphone intervention, such as schedule routine measurement and duration of each measurement. Moreover, the firmware of the ring can also be updated wirelessly, such as when paired with the smartphone 300. The microcontroller is also in change of the power management of the whole ring. When in sleep mode, it will power down the analog front end 200 to saving power, and will also bypass the power system 110 and connect itself directly to the battery to minimize the power consumed by the power system. When woken up, the power system 110 will turn on to regulate the power supply to the whole ring. However, the analog front end 200 will be kept powered down until the ECG measurement is ready to be conducted.

During an ECG measurement, the microcontroller 120 will perform analog to digital conversion periodically according to the sampling rate and either save the data in the on-chip flash or through the air via Bluetooth Low Energy. One example of a microcontroller 120 is the Texas Instrument (TI) cc2541 SimpleLink Bluetooth Smart and Proprietary Wireless MCU. It combines the Bluetooth module and an 8051 microcontroller in a single chip. Its small footprint and excellent power management makes it very suitable for a wearable device. The successor of it, cc2640 will be a better choice in the term of power saving and footprint. The Bluetooth Low Energy Generic Access Profile (GAP) layer provides some APIs for control of connection, such as establish and termination of the connection, and other connection details, such as connection interval. The microcontroller 120 controls the control interval to balance the data transmission rate and power consumption. This is also part of the power management, but more specific for the wireless communication (e.g. Bluetooth Low Energy) part.

Analog Front End (AFE) System 200

Figure 7:
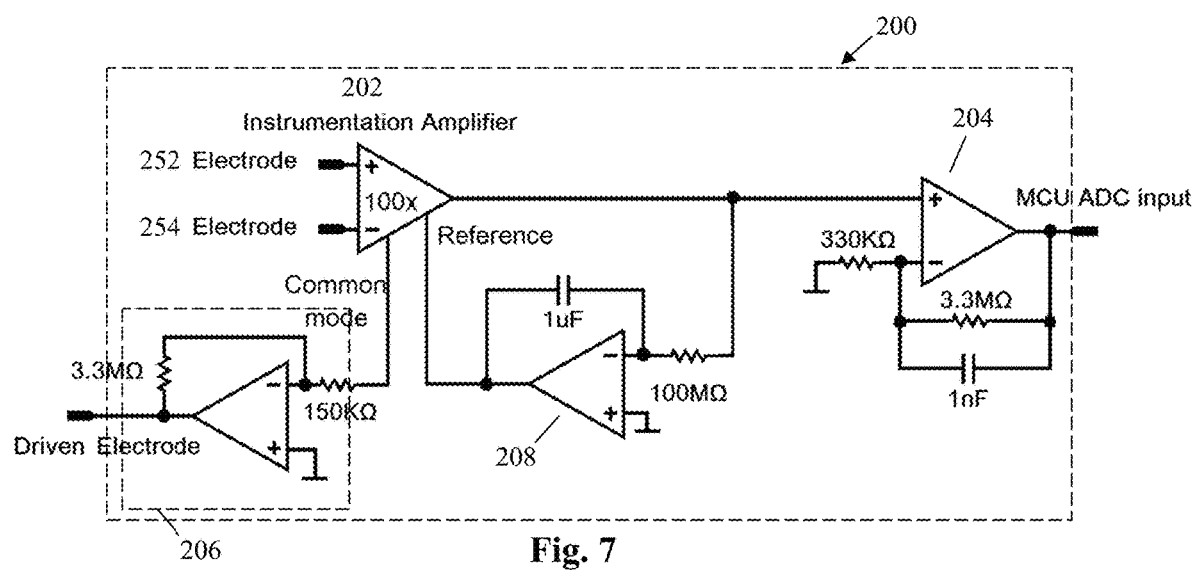
FIG. 7 is a circuit diagram for the ECG analog front end.

In a non-limiting illustrative embodiment of the invention, FIG. 7 shows an example ECG signal conditioning AFE system 200, which includes an instrumentation amplifier 202, a low frequency noise feedback circuit 208, a second stage amplifier 204, and a driven electrode (also called driven-right-leg) circuit 206. The gain of the instrumentation amplifier 202 has a fixed gain of 100 (although can be other values between 10-1000 depending on the application), and has a DC blocking (high-pass) filter, of which the cut off frequency can be set to 0.04 Hz. The second stage amplifier 204 is set to have a gain of 10, and also works as a low pass filter of a cutoff frequency ranging from 40-150 Hz. As a result, the total gain is 1000, and the passband frequency is 0.0440 or 0.04-150 Hz depending on applications. Commercial ECG analog front end (AFE) chip such as AD8232 from Analog Device can be used for the ECG signal acquiring and conditioning. The output of the AFE 200 is connected to an analog-to-digital converter (ADC) (e.g. an MCU analog input), which can be part of the microcontroller 120.

The AFE 200 receives the analog voltage signal from the electrodes 250, filters that signal (e.g., band-pass filter it between 0.05-150 Hz), and then sends the filtered signal to an ADC. The electrodes 252, 254 are connected to the input of the instrumentation amplifier 202. The electrodes 252, 254 can be made of stainless steel, or conductive nanoparticle (Ag, Au, etc.) doped PDMS, or gel coated Silver/Silver Chloride electrodes. The electrodes 252, 254 are located and exposed on either the inner or outer surface of the ring. The electrodes 252, 254 are able to obtain a reliable signal from the body without having to use a gel because they are on a finger ring and can be actively pressed onto the body by the user and maintain good contact with the body. In addition the soft substrate helps buffer the relative movement between the electrodes and the body, which can reduce motion artifacts.

The driven electrode circuit 206 sends a small feedback current into the patient's body through the driven electrode, effectively grounds the body, removes common mode interferences and also provides some protection to the patient by limiting the current into the body. The instrumentation amplifier 202 extracts the common mode part from the input signal and provides it to the driven electrode circuit 206. The driven electrode circuit 206 buffers, inverts, and amplifies the common mode signal and feeds the amplified and inverted signal back to the human body to suppress the common mode interference. The operational amplifier, 100 MOhm resistor and 1 uF capacitor form a low frequency noise feedback circuit 208. This circuit picks up the low frequency noise at the output of the instrumentation amplifier 202, and feed the noise back to the instrumentation amplifier 202 in order to block the low frequency noise. The combination of 202 and 208 forms a DC blocking (high-pass) filter. The instrumentation amplifier 202 output forms an input to the second stage amplifier 204. The output of the second stage amplifier 204 forms an output for the AFE 200.

Wireless Communication Subsystem

In a non-limiting illustrative embodiment of the invention, the ring 100 can have a wireless communication subsystem that is connected to or integrated with the MCU 120. The wireless communication subsystem can be Bluetooth Low Energy (BLE). In a BLE implementation, most of communications or data exchange between the ring 100 and the smartphone 300 can be through the Generic Attribute Profile (GATT) layer. For example, the ring device works as a GATT service, which provides the data to the client, and the smartphone works as a GATT client, which can access and modify the parameters and settings on the ring device. The ECG data, the device status and all the settings controllable by the smartphone, such as measurement duration are exposed to the smartphone as a specific GATT service. Each data, status, or setting is represented as an attribute in the service attribute table. By reading corresponding attribute of the status, for example the status of analog frontend, we can know whether the analog frontend is powered on or not, and whether the electrodes is attached to the user body or not. By writing to the setting attribute, such as the start measurement attribute, we can start a measurement. The ECG data attribute can be a notification enabled attribute. This type of attribute will push the data to the smartphone, when a new data comes, without the smartphone actively reading the data, which is suitable for continuous data transmission controlled by the GATT server side, i.e. the ring side.

The Electrode Subsystem 250

Figure 3:
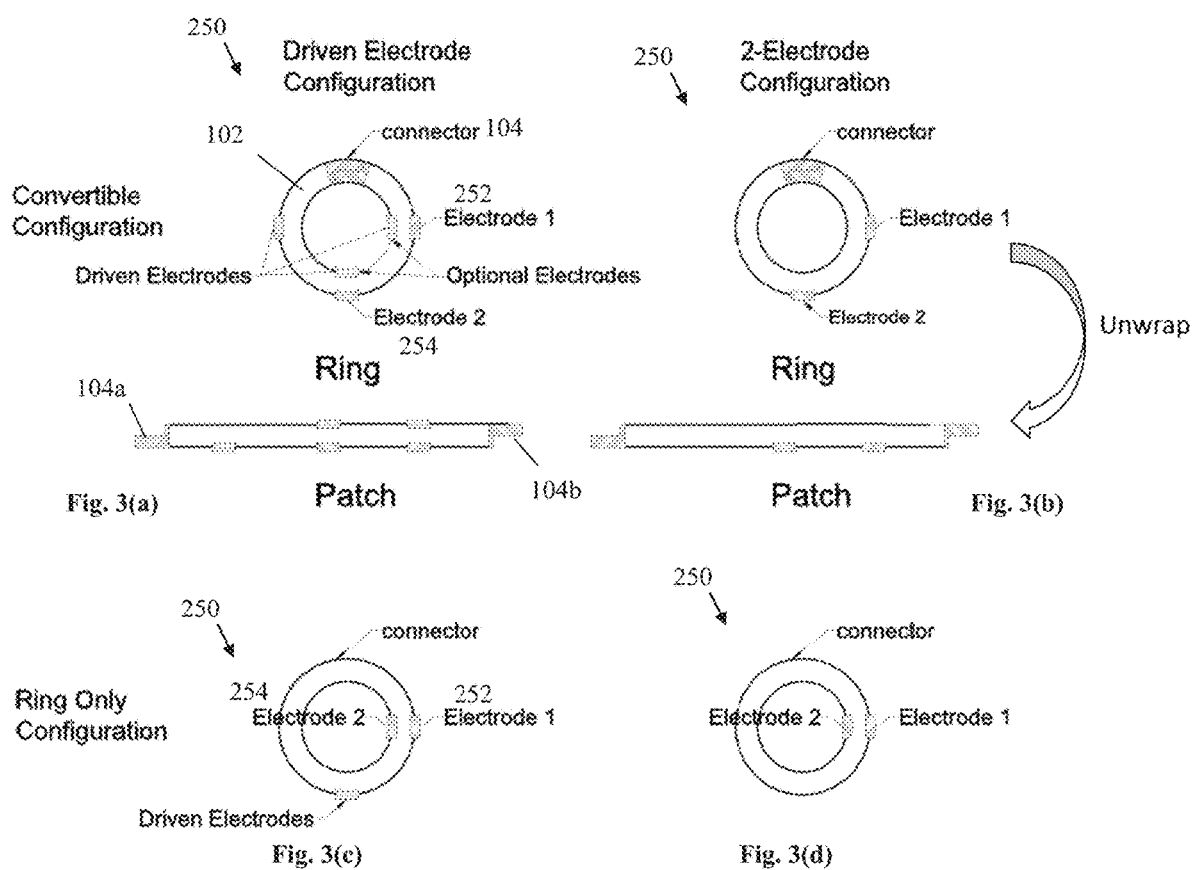
FIGS. 3(a)-(b) show different configurations where the device can be converted between a ring and a patch.
FIGS. 3(c)-(d) show different configurations for the ring only embodiments of the invention.

FIG. 3 shows various non-limiting illustrative configurations for the electrode subsystem 250 of the present invention. FIGS. 3(a) and 3(b) show embodiments where the ring 100 has a connector 104 that can be used to open the ring 100, where the ring 100 is flexible; and FIGS. 3(c) and 3(d) show embodiments without the connector, with the sensor 100 having the shape of a ring. The connector 104 can be any suitable fastener that enables one end of the ring to be removably connected to an opposite end of the ring, such as a latch and hub. In the embodiments shown in FIGS. 3(c) and 3(d), the connector 104 has a first mating connector 104a that can be removably interlocked with a second mating connector 104b. For instance, the mating connectors 104a, 104b can be permanent magnets that attract each other when brought close together and form a connection.

When the connector 104 is locked, the sensor 100 has a ring shape. When the connector 104 is unlocked, the sensor 100 can be flattened to a substantially linear shape (since the sensor 100 is flexible) that conforms with the patient's body, and can be used as a patch that can be applied to the patient's body. However, the sensor 100 is generally referred to as a "ring" in this application, whether in the circular ring configuration or the linear patch configuration.

As shown, the ring 100 can have two or more electrodes 250. The ring is a flat thin elongated body or substrate 102 that is formed of flexible material, as described in U.S. Pat. No. 9,116,145, which is herein incorporated by reference. The electronic components (including the power supply 110, MCU 120, AFE 200, and electrodes 250) are small and embedded (fully encased) in the substrate 102, so that the ring 100 can be flexed and bent into the ring shape configuration or the flat patch configuration. Except that a top surface of the electrodes 250 is exposed at and flush with the top surface of the substrate 102. In one exemplary embodiment, the largest component is the MCU, which is typically 4 mm by 4 mm by 0.8 mm in size. All other components are smaller.

In FIG. 3(b), a first electrode 252 can be located at a first side (i.e., at the outer surface or outer side when in the shape of the ring) of the substrate 102, and a second electrode 254 can be located at that same first side of the substrate 102, but offset to one side. In this manner, one or both electrodes 252, 254 can be pressed against the body of the patient. Or as shown in FIG. 3(d), the second electrode 254 can be at a second opposite side (i.e., at the inner surface or inner side when in the shape of the ring) of the substrate 102, and the first electrode 252 can be aligned with the second electrode 254. In this embodiment, the first electrode 252 can be pressed to one part of the body (FIG. 1), and the second electrode 254 is pressed against the patient's finger and can take a measurement from the patient's finger.

Referring to FIGS. 3(a), 3(c), additional electrodes can be optionally be provided at the first side and/or a second opposite side (the outer side when in the shape of the ring) of the substrate 102, including driven electrodes. The optional electrode can function as a driven electrode to reduce common-mode interference. A driven electrode is for reducing common-mode interference. As shown, the driven electrode(s) can be aligned with a respective first electrode 252 and/or second electrode 254, or the driven electrode(s) or an additional driven electrode(s) can be offset from the first and/or second electrode 254. It should be noted that even where additional electrodes are provided, not all of the electrodes need to be operated. For instance, in the embodiment of FIG. 3(d), the first electrode 252 can be inactive and only the second electrode 254 be used to take a measurement, such as at various times determined by the MCU 120, either with or without knowledge of the patient.

Further to one illustrative, non-limiting embodiment of the invention, one electrode should always be on the outside surface of the ring in order to get in contact with different parts of the body. The other electrodes can be either on the outside surface or the inside surface, as given in FIGS. 3(a)-(d). They are just different implantations and have different complexity levels. The driven electrodes can be on either side. The electrodes 250 can be exposed at the inner or outer surfaces of the ring so that their conductive surfaces can be in physical contact with the body.

The electrodes 250 used in the ring can be stainless steel, conductive PDMS electrodes with nano conductive particle mixed in it, or traditional Ag/AgCl gel electrodes. Stainless steel electrodes are durable, reliable, easy to make, and low cost. PDMS electrodes are more conformal to the skin, comfortable. The gel electrodes provide a better signal to noise ratio. The device can use two electrodes setup for simplicity or three electrodes setup for better signal to noise ratio.

The Power Subsystem 110

In a non-limiting illustrative embodiment of the invention, the power system 110 has a power source (e.g. rechargeable lithium coin battery, or a super capacitor, or a solar cell), and a power regulator with passive components, which provides a constant voltage during the battery's life time. A constant voltage helps the microcontroller working reliably and can also work as a reference voltage for the analog to digital conversion (ADC) unit. The regulator provides a voltage typically lower than the 3V from the lithium battery. Since the BLE controller we used consumes a fairly constant current in its recommended operating supply range, a low supply voltage will further reduce the power consumption. Since the regulator will consume power as well, the regulator must have bypass function, so in the case of the whole ring is in the ultra deep sleep mode, in which power consumption of the power regulator is comparable or even larger than the rest of system, the regulator can be powered down or bypassed to minimize the power consumption. An example power regulator is TI TPS62730 for cc2541 and, TPS62740 for cc2640. For our ring with cc2541 microcontroller, the working current is about 3 mA in average, and the sleep current is less than 1.5 uA. For a usage scenario including 8 measurements per day and 30 s duration per measurement, the average current is 9.8 uA. With a Sony CR1220 battery of 40 mAh capacity, our ring can last about 170 days. If taking off the ring for recharging is not desirable, flexible solar cells can be used as the power source.

The Software Subsystem

In one non-limiting illustrative embodiment of the UI device 300, a smartphone with a custom application can configure the measurement settings like sampling rate and measurement duration, upload the saved data from the ring to the smart phone, or initial a real time measurement, and display this real time ECG graph, when the ring sensor 100 is paired with the phone device 300. When the ring 100 is offline, the app can be used to view saved ECG graphs, and to conduct some more sophisticated analysis. The measured data can be uploaded to the cloud via the Internet to keep a record of the user's heart hearth over time, if it is permitted by the user. If the app finds any irregularity during the analysis, the patient device 300 can send data (e.g. by email or phone call) to user's physician for further analysis. If the diagnosis algorithm (either in the cloud or on the UI device) is sufficiently accurate, the ring 100 can contact the emergency response organization immediately, if any serious symptom is found during real time measurement.

The Fabrication Process (FIG. 6)

As noted above, the ring device 100 can be fabricated using the soft electronics/microfluidics co-packaging technique, which offers maximum mechanical flexibility and softness. The physical structure of the ring device can be one of the two possible configurations, shown in FIG. 5(a) or FIG. 5(b). The detailed fabrication steps for configuration one are given below and shown in FIG. 6.

Starting at FIG. 6(a), step 1A, the electronic components 105 are placed at the corresponding positions on the mold 106. The electronic components include all of the components for the power 110, Wireless and MCU 120, AFE 200, and electrodes 250. At step 1B, the packaging material 108 is added to form the embedded electronics layer. The packaging material 108 is flexible (and forms substrate 102 (FIG. 3)), and can be PDMS, an elastomer, or it can be other elastomers such as fluoro-elastomer. The spacing between components are typically several (2-5) times larger than the component size so that the device remain flexible. This step fully embeds the electronics in the packaging material 108 (i.e., substrate 102) so that the electronics are completely surrounded by the packaging material 108, except that one surface of the electrodes 250 is exposed at the surface of the material 108. Thus, all the sides and bottom of the electrodes 250 are surrounded by the packaging material 108, and the top surface of the electrodes 250 is exposed at and flush with the top surface of the packaging material 108. At step 1C, the packaging material 108 and combined electronics layer is peeled off from the mold 106, which leaves just the embedded electronics layer 112.

Turning to FIG. 6(b), step 2A, packaging material is added on to a mold 107 to form a flexible contact via layer having contact vias that extend through the packaging material. At step 2B, the contact via layer is peeled off from the mold 107. The vias in the contact via layer will be aligned and connected with the contact pads of the IC chips allowing the injection of liquid conductive material to form electrical interconnects among ICs, passive components and electrodes etc.

Turning to FIG. 6(c), step 3A, packaging material is placed onto a mold 113 to form the interconnect layer 114. The interconnect layer 114 is a layer with injection via and/or interconnect channels which will allow the injection of liquid conductive material and form electrical interconnects among electronic components. At step 3B, the interconnect layer 114 is peeled off from the mold 113. At step 3C, the interconnect layer 114 is flipped over.

Figure 6D:
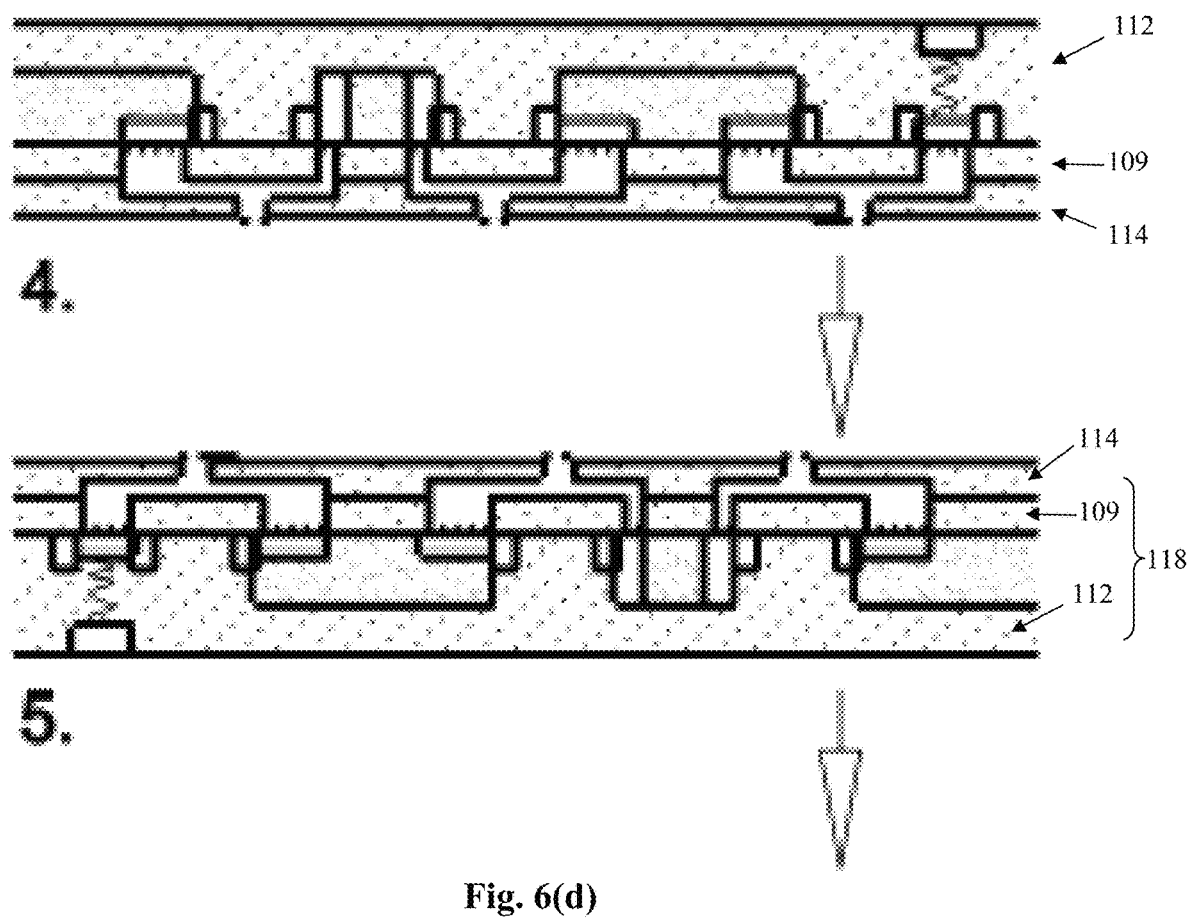
Figure 6F:
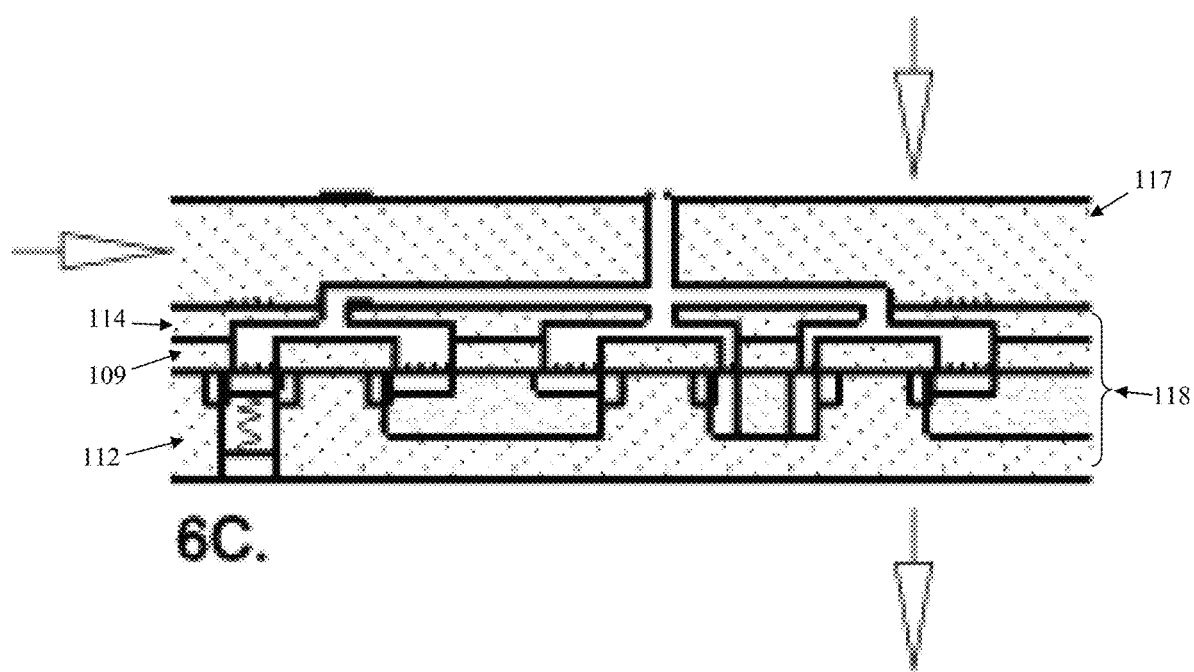

Turning to FIG. 6(d), step 4, the embedded electronics layer 112, contact via layer 109 and the interconnect layer 114 (from steps 1-3 above) are aligned and bonded together. The embedded electronics layer 112 forms the top layer, the contact via layer 109 forms a middle layer and the interconnect layer 114 forms a bottom layer. The two layers can be bonded by $O_2$/air plasma activation. The surfaces of the two layers are treated with $O_2$ or air plasma for 10-30 seconds and brought into contact with each other. The baking in an 80 degree C. oven will form a permanent bond. The two layers can be manually aligned under a stereoscope, or automatically aligned by using a pick-and-place machine or a mask aligner. The contacts on the contract via layer 109 will be aligned with the via on the interconnect layer 114. The majority of the two layers is PDMS elastomer, and other components in the two layers can be semiconductor Silicon, or ceramic or metal. The bonding is mainly due to PDMS to PDMS (or elastomer to elastomer) bonding.] At step 5, the device 118 is flipped over.

Figure 6G:
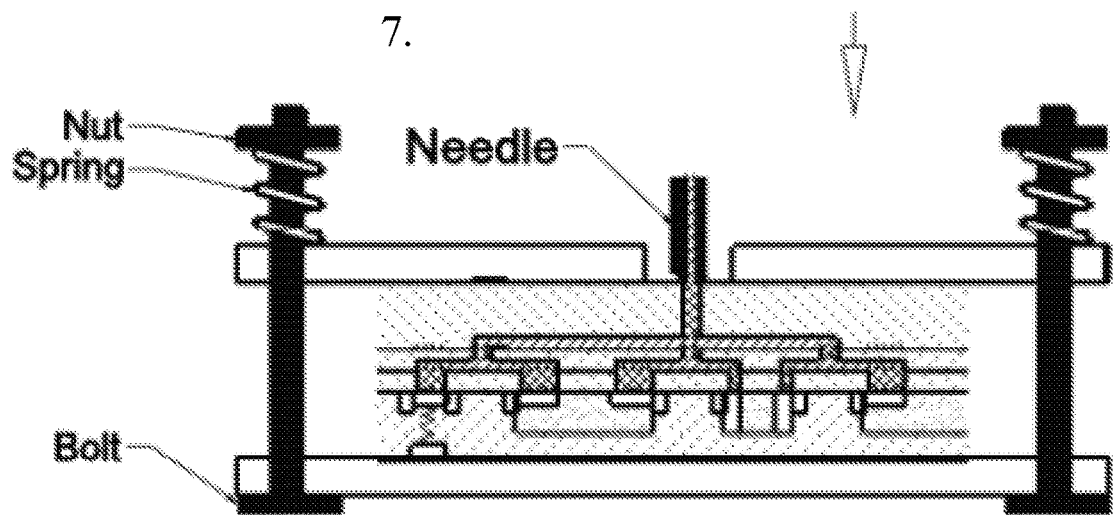
Figure 6H:
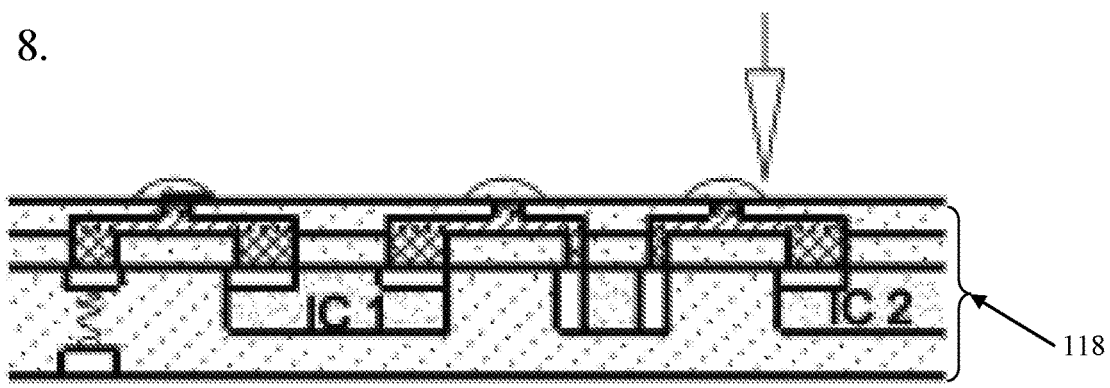

Referring to FIG. 6(e), step 6A, packaging material is added on to another mold 116 to form an injection layer 117. At step 6B, the injection layer is peeled off of the mold 4. At FIG. 6(f), step 6C, the injection layer is aligned on top of the device from step 5 without bonding. In FIG. 6(g), step 7, the injection layer 117 is tightly and evenly clamped to the bottom, using a station composed of board, bolts, and spring. At FIG. 6(h), conductive material is injected into the openings in the injection layer 117. The injection layer 117 is for injecting liquid conductive material for form interconnects. The injection layer 117 has only one opening and a network of channels connected to the injection via in the interconnect layer 114. At step 8, the injection layer 117 is removed, and the injection opening is cleared and sealed.

Figure 5A:
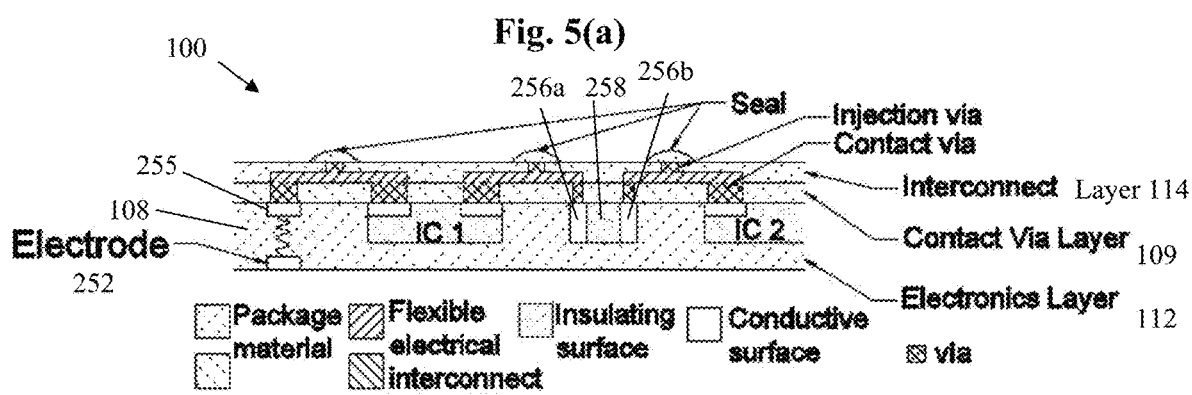
FIGS. 5(a), (b) are block diagrams showing two different configurations for the ring device structure.

The device shown in FIG. 5(a) is prepared by the process of FIGS. 6(a)-(h). IC1 and IC2 are integrated circuit chips such as the microcontrollers 120, AFEs 200, MEMS chips, optoelectronic chips etc. The packaging elastomer materials (such as PDMS or fluoroelastomers), and flexible conductive interconnects (such as liquid metal or silver nanoparticle doped PDMS) are bendable and stretchable, whereas the IC chips and discrete components (resistors, capacitors, inductors etc.) are typically rigid. Thus, all the components are flexible (including the packaging materials and the various channels and vias), except for the electronic components. The final device consists mainly of the flexible materials with rigid components embedded so that the final device is still flexible (i.e., bendable and stretchable to certain degree and the rigid components sufficiently small and spaced apart so as not to effectively diminish the flexibility).

Accordingly, as shown in FIG. 5(a), the ECG sensor 100 has an electronics layer 112 at the bottom that forms the main layer. The microcontroller 120, AFE 200 and other electronics such as a resistor 258, are embedded in the packaging material (or substrate) 108 of the electronics layer 112, with the top surface of the electronics 120, 200, 258 flush with the top surface of the internal side of the packaging layer 108. An outer electrode 252 (or it can be an inner electrode 254) is also shown embedded in the packaging layer 108 with the top surface of the electrode 252 flush with and exposed at the outer surface of the packaging layer 108. The bottom or inner electrode 254 can be connected by a wire that extends through the packaging layer 108 to an internal conductive contact or connection point 255 which is connected to the input conductive contact of the AFE, represented here by IC1.

As further shown, other electronic components, such as a passive resistor 258 can be embedded in the electronics layer 112. The resistor 258 has a first conductive contact 256a at one side and a second conductive contact 256b at an opposite side. The contacts 256a, 256b are flush with the top surface of the packaging material 108 of the electronics layer 112, so that they are exposed at the electronics layer 112 and electrical contact can be made with those elements. The resistor 258, as well as IC1, IC2, are also shown flush with the top surface of the packaging material. However, the resistor 258, IC1, IC2 need not be flush with the top surface, as long as their respective contacts are exposed at the electronics layer 112.

The contact via layer 109 is positioned above the electronics layer 112 and the contact vias are aligned with the passive component leads or contacts 255, 256a, 256b and with the conductive contact pads of the ICs.

The interconnect layer 114 is positioned above the contact via layer 109 with interconnect channels aligned with the contact vias of the contact via layer 109, and the injection via in communication with the interconnect channels. Accordingly, the injection via is in flow communication with the contact vias, by way of the interconnect channels. In this way, a liquid conductive material can be filled into the electronics layer 112 to form the interconnects among the electrodes 252, 254, the contact leads of passive components and the conductive contact pads for the integrated circuits IC1, IC2. Once those are filled, the injection via is sealed and the liquid conductive material can be solidified or sealed within.

Accordingly, the electronic components in the electronics layer 112, namely IC1, IC2, electrode contact 255, and resistor 258, are fully embedded in the substrate that is formed by the packaging layer 108 of the electronics layer 112, the packaging layer of the contact via layer 109, and the packaging layer (and seal) of the interconnect layer 114. None of those electronic components are exposed from the ECG sensor 100. Only one surface of the electrode 252 is exposed from the ECG sensor 100, as shown.

Three interconnect channels are illustrated in FIG. 5(a). The first interconnect channel has a first end that connects to a first contact via and a second end that connects to a second contact via. The first contact via connects to the electrode contact 255 and the second contact via connects to the IC1 input contact, so that the first and second contact vias and the first interconnect channel electrically couple the contact 255 to the IC1 input contact. The second interconnect channel has a first end that connects to a third contact via and a second end that connects to a fourth contact via. The third contact via connects to the IC1 output contact and the fourth contact via connects to the resistor input contact 256a, so that the third and fourth contact vias and the second interconnect channel electrically couple the IC1 output contact to the resistor input contact 256a. The third interconnect channel has a first end that connects to a fifth contact via and a second end that connects to a sixth contact via. The fifth contact via connects to the resistor output contact 256b and the sixth contact via connects to the IC2 input contact, so that the fifth and sixth contact vias and the third interconnect channel electrically couple the resistor output contact 256b to the IC2 input contact.

Thus, the electrode 252 is connected to the contact 255 by a wire. The contact 255 is connected to the IC1 input contact by the conductive material in the first contact via, the first interconnect channel and the second contact via. The IC1 output contact is connected to the input contact 256a of the resistor 258 by the conductive material in the third contact via, the second interconnect channel, and the fourth contact via. And, the resistor output contact 256b is connected to the input contact of IC2 by the conductive material in the fifth contact via, the third interconnect channel, and the sixth contact via. Of course, further electrical components can be included in the electronics layer 112, and further contacts made by the contact via layer 109 and interconnect layer 114.

Thus, the electronics layer has an outer surface at which the electrode 252 is formed, and an inner surface. The contact via layer has a first surface in direct contact with the inner surface of said electronics layer. The contact via layer has a second surface opposite the first surface. The interconnect layer has an inner layer in direct contact with a second surface of the contact via layer. And the interconnect layer has an outer surface at which the seal is placed. All of the layers are thin, having uniform thickness, and elongated and their surfaces can be continuous (without gaps) to form a sealed ECG sensor 100 that cooperate to fully embed the electronic components 255, IC1, IC2, 258, as well as the conductive material in the contact vias, interconnect channels, and injection via.

Figure 4:
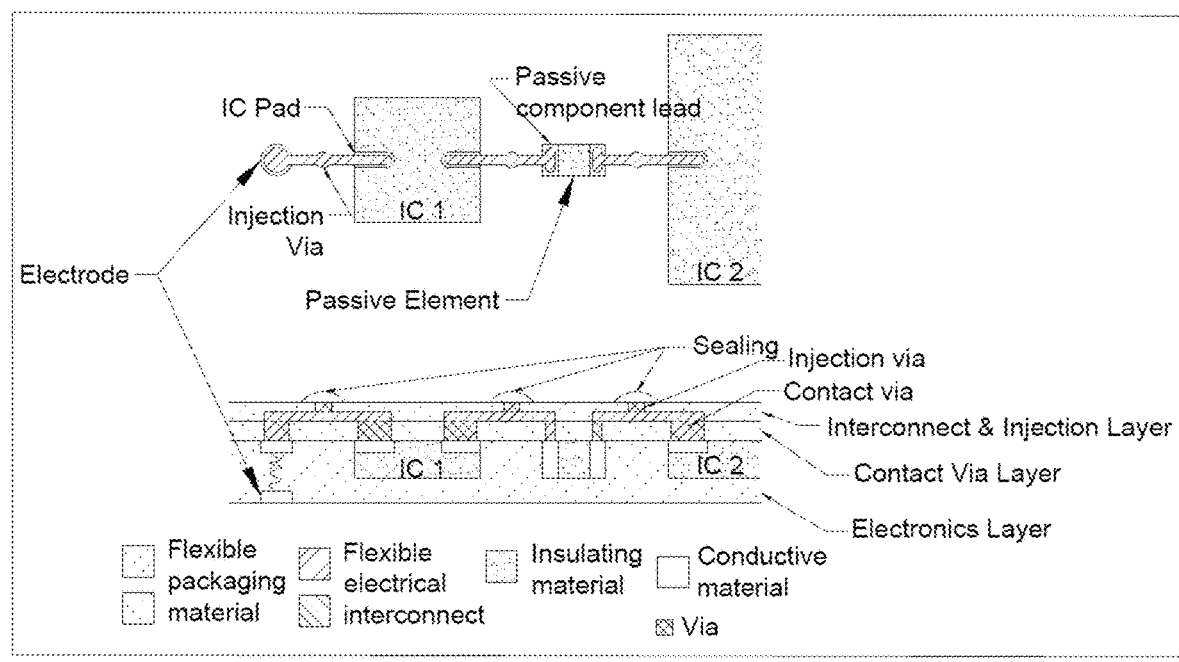
FIG. 4 is a block diagram showing the ring device structure, before bending into a ring.

FIG. 4 shows both the top-view (top) and cross-sectional view (bottom) of the device 100. The top view shows how the flexible interconnects links the IC pads and passive components leads.

Figure 5B:
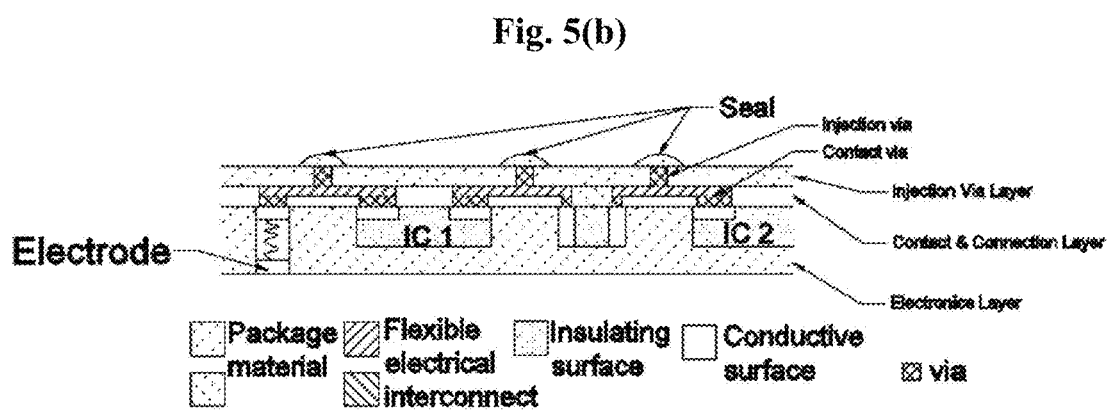

FIG. 5(b) is an alternative manufacturing process to further illustrate the scope of the invention. Here, the injection vias and interconnect channels are no longer in a single layer 114 as in FIG. 5(a). Instead the injection vias and interconnect channels are located in two separate layers and the interconnect layer also contains contact vias to the IC chips.

Figure 9:
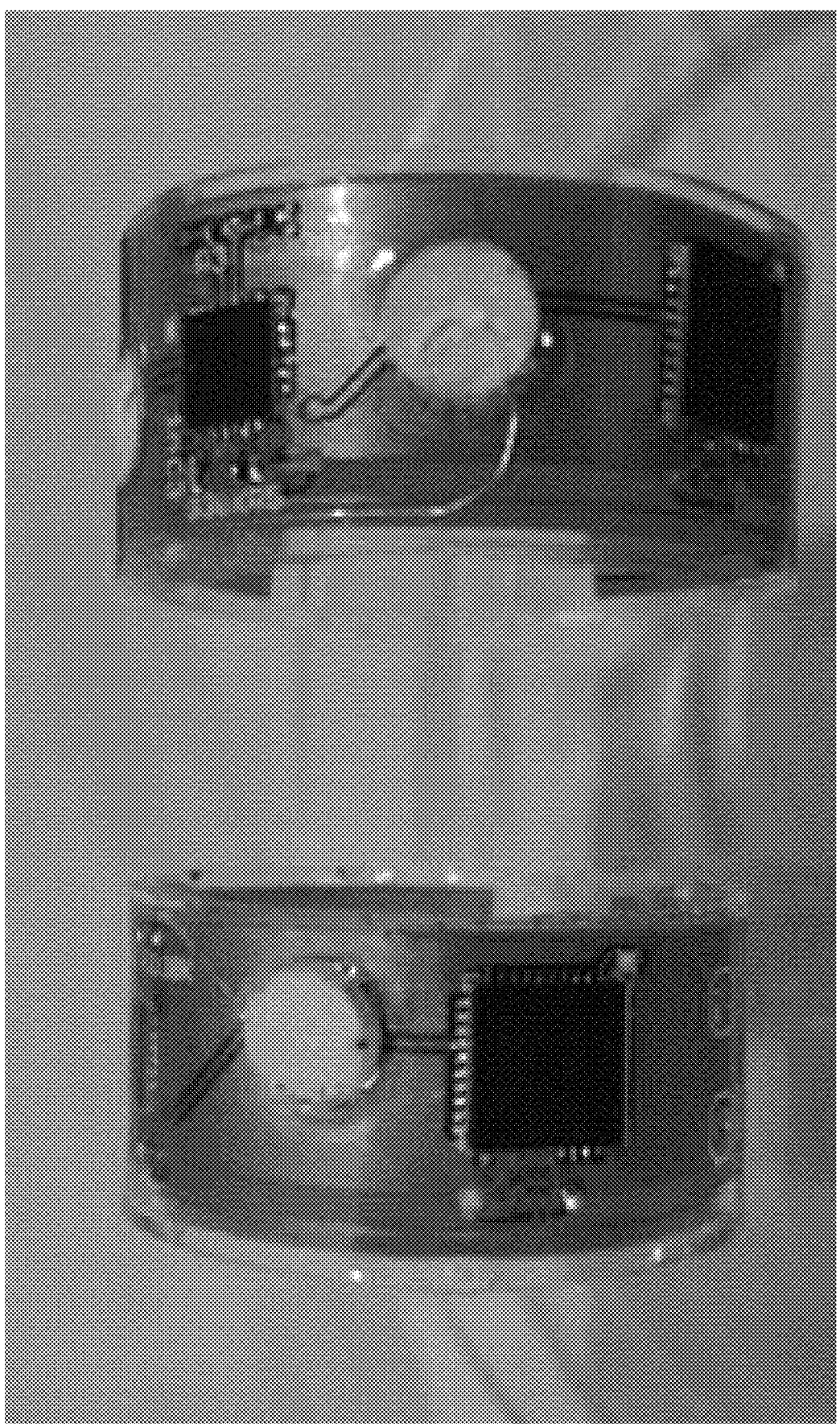
FIG. 9 are pictures of the ECG ring sensors in nonlimiting illustrative embodiments.

Another fabrication method is to use a traditional flexible printed circuit board (PCB) for the circuit, package the circuit into ring shape, then assemble the electrodes and battery. FIG. 9 shows two example ring sensors fabricated by this alternative method.

The packaging materials (for steps 1B, 2A, 3A, 6A) can be elastomer, such as polydimethylsiloxane (PDMS), fluoroelastomer, polyurethane for flexibility. Injection molding plastic can be also used for hard rings. In the hard ring case (FIGS. 3(c), 3(d)), the ring must be composed of several segments which are connected flexibly if it is still needed to be unwrapped into a patch format (FIG. 3). The ring can be made of metal, which will look more like a normal ring. In this case, the electrodes need to be proper isolated with each other and the remaining surface of the ring.

Application

The ring ECG 100 is mainly developed for on-demand real-time ECG measurement for those who want to keep track of heart health, and those with heart attack potentials who want to measure their heart activity to do some early diagnosis in order to take early response when feeling uncomfortable. However, the measurement of ECG can be used with other vital signs to get more about information about personal health. The ECG signal combined with pulse oximetry can give out the blood pressure after calibration with each individual, and the pulse oximeter can be integrated onto the ring. In the situation where a ring is on the finger and continuously measures the oximetry and a patch unwrapped from the ring is placed and fastened on the chest, the ECG and/or blood pressure can then be continuously measured after calibration. FIG. 8(b) shows that the ECG measurement taken by the present invention is substantially the same as a conventional ECG measurement (FIG. 8(a)).

The user wearing a ring ECG sensor can touch the exposed ECG electrode to different locations on the body to obtain multiple lead ECG signals (e.g. traditional 12-lead ECGs) at different times. Or the user can wear multiple rings so that each ring can touch a distinct location on the body to acquire simultaneous multi-lead ECG signal measurements.

The description uses several geometric or relational terms, such as circular, ring, and flat. In addition, the description uses several directional or positioning terms and the like, such as top, bottom, inner, and outer. Those terms are merely for convenience to facilitate the description based on the embodiments shown in the figures. Those terms are not intended to limit the invention. Thus, it should be recognized that the invention can be described in other ways without those geometric, relational, directional or positioning terms. In addition, the geometric or relational terms may not be exact. And, other suitable geometries and relationships can be provided without departing from the spirit and scope of the invention. For instance, the ECG sensor 100 can be made into a necklace or other wearable device, such as a wristband, watch, glove or clothing, especially in those embodiments where no inside electrode is needed.

The system and method of the present invention include operation by a one or more processing devices, including the MCU 120 and a processing device in the patient device 300. It is noted that the processing device can be any suitable device, such as a processor, microprocessor, PC, tablet, smartphone, or the like. The processing devices can be used in combination with other suitable components, such as a display device (monitor, LED screen, digital screen, etc.), memory or storage device, input device (touchscreen, keyboard, pointing device such as a mouse), a wired and/or wireless module (for RF, Bluetooth, infrared, WiFi, Zigbee, etc.). The information may be stored on a computer hard drive, on a CD ROM disk or on any other appropriate data storage device. The entire process is conducted automatically by the processing device, and without any manual interaction. Accordingly, the process can occur substantially in real-time without any delays.

It should also be appreciated that while the sensor 100 is used in connection with a patient mobile device 300, the mobile device 300 can be optional and need not be present for the sensor 100 to take ECG measurements and analyze the information. In addition, some or all of the operation of the mobile device 300 can be implemented in the sensor 100. And, some of the operation of the sensor 100 can be performed at the mobile device 300, such as analyzing the data.

It is further noted that all of the embodiments of the ECG sensor 100 shown and described herein are flexible, including the rings shown in FIGS. 3(a)-(d). However, a rigid ECG sensor 100 can also be provided within the spirit and scope of the invention, such as for instance the rings 100 of FIGS. 3(c)-(d) that do not have a connector and do not convert from a circular ring into a linear patch.

The following documents are incorporated herein by reference: [1] Drew, Barbara J., et al. "Practice Standards for Electrocardiographic Monitoring in Hospital Settings An American Heart Association Scientific Statement From the Councils on Cardiovascular Nursing, Clinical Cardiology, and Cardiovascular Disease in the Young: Endorsed by the International Society of Computerized Electrocardiology and the American Association of Critical-Care Nurses." Circulation 110.17 (2004): 2721-2746. [2] Chi, Yu M., and Gert Cauwenberghs. "Wireless noncontact EEG/ECG electrodes for body sensor networks." Body Sensor Networks (BSN), 2010 International Conference on. IEEE, 2010. [3] I D. Ruehlemann, K. Kuegler, B. Mydlach and P. J. Frosch. "Contact dermatitis to self-adhesive ECG electrodes," Contact Derm. 62(5), pp. 314-315. 2010. [4] Zhang, Bowei et al. Flexible packaging of solid-state integrated circuit chips with elastomeric microfluidics. Scientific Reports, 3: 1098, 2013. [5] Paddy M. Barrett, et al. "Comparison of 24-hour Holter Monitoring with 14-day Novel Adhesive Patch Electrocardiographic Monitoring", Am J Med. 127(1):95, e11-7, January 2014. [6] Kristian Thygesen, et al. "Third Universal Definition of Myocardial Infarction", J Am Coll Cardiol. 60(16):1581-1598, 2012.

Within this specification, the terms "substantially" and "about" mean plus or minus 20%, more preferably plus or minus 10%, even more preferably plus or minus 5%, most preferably plus or minus 2%.

Within this specification embodiments have been described in a way which enables a clear and concise specification to be written, but it is intended and will be appreciated that embodiments may be variously combined or separated without departing from spirit and scope of the invention. For example, it will be appreciated that all preferred features described herein are applicable to all aspects of the invention described herein.

The foregoing description and drawings should be considered as illustrative only of the principles of the invention. The invention may be configured in a variety of shapes and sizes and is not intended to be limited by the preferred embodiment. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

The invention claimed is:

1. An electrocardiogram (ECG) sensor comprising:
   a flexible thin ring-shaped substrate configured to be worn about a finger of a patient, said substrate having an inner surface and an outer surface opposite the inner surface, wherein said substrate is bendable and stretchable;
   at least one connector having a locked position to lock the substrate in a ring shape, and an unlocked position whereby the substrate has a substantially linear shape that is configured to attach by gel to and conform with a body of the patient as a wearable patch;
   a first ECG electrode positioned at the outer surface of said substrate; and
   a second ECG electrode positioned at the inner surface of said substrate configured to be in contact with the finger of the patient, whereby the first and second ECG electrodes receive a single-lead ECG signal when the first ECG electrode is touched to the body of the patient,
   wherein touching the first ECG electrode to different locations on the body of the patient at different times provides asynchronous multi-lead ECG measurements.

2. The sensor of claim 1, further comprising multiple ECG sensors; wherein touching the first ECG electrode of each of the multiple ECG sensors to different locations on the body of the patient at the same time provides simultaneous multi-lead ECG measurements.

3. The sensor of claim 2, further comprising a processing device mounted to said substrate and configured to provide the asynchronous and the simultaneous multi-lead ECG measurements.

4. The sensor of claim 1, further comprising a sensor processing device configured in the ECG sensor with said first and second ECG electrodes to receive the signal from the ECG sensor, configure the received signal and transmit the signal to a remote mobile device.

5. The sensor of claim 4, further comprising the remote mobile device, said remote mobile device having a remote processing device configured to receive the signal from the ECG sensor and process the received signal.

6. The sensor of claim 1, further comprising a processing device configured to receive the signal from the ECG sensor, analyze the signal and contact an emergency service in response to the analyzed signal.

7. The sensor of claim 1, wherein the first and second ECG electrodes are embedded in said substrate with a top surface of each of said first and second ECG electrodes exposed at and flush with a top surface of said substrate.

8. The sensor of claim 1, wherein the first and second ECG electrodes are pressed to the body of the patient to detect the ECG signal from the body of the patient without use of a gel.

9. The sensor of claim 1, further comprising a sensor processing device configured in the ECG sensor with said first and second ECG electrodes to receive the ECG signal from the first and second ECG electrodes; and further comprising a liquid conductive material embedded in said substrate to electrically couple said sensor processing device with said first ECG electrode and with said second ECG electrode.

10. An electrocardiogram (ECG) sensor comprising:
    a flexible elongated substrate having an inner surface and an outer surface opposite the inner surface, said substrate having a first end and a second end opposite the first end wherein said substrate is bendable and stretchable;
    a first connector at the first end of said substrate;
    a second connector at the second end of said substrate, whereby the first and second connectors can be removably engaged and have a first locked position wherein the first and second connectors are locked and the substrate is in a ring shape configured to be worn about a finger of a patient, and a second unlocked position wherein the first and second connectors are disengaged and the flexible substrate is in a substantially linear shape and is bendable and stretchable and configured to be attached by gel to and conform with a body of the patient as a wearable patch; and
    a first ECG electrode positioned at the inner surface of said substrate, whereby the ECG electrode receives an ECG signal when touched to the body of the patient,
    a second ECG electrode positioned at the outer surface of said substrate and the first ECG electrode is in contact with the finger of the patient, whereby the first and second ECG electrodes receive a single-lead ECG signal when the second electrode is touched to the body of the patient,
    wherein touching the second ECG electrode to different locations on the body of the patient at different times provides asynchronous multi-lead ECG measurements.

11. The sensor of claim 10, further comprising multiple ECG sensors, wherein touching the second ECG electrode of each of the multiple ECG sensors to different locations on the body of the patient at the same time provides simultaneous multi-lead ECG measurements.

12. The sensor of claim 10, further comprising a sensor processing device configured in the ECG sensor with said first and second ECG electrodes to receive the ECG signal from the first and second ECG electrodes; and further comprising a liquid conductive material embedded in said substrate to electrically couple said sensor processing device with said first ECG electrode and with said second ECG electrode.

13. An electrocardiogram (ECG) sensor comprising:
an electronics layer having a first flexible packaging layer with an inner surface, wherein said first flexible packaging layer is bendable and stretchable;
a first electronic component having a first conductive contact, said first electronic component embedded in the first flexible packaging layer with at least a portion of the first conductive contact exposed at the inner surface of the first flexible packaging layer;
a second electronic component having a second conductive contact, said second electronic component embedded in the first flexible packaging layer with at least a portion of the second conductive contact exposed at the inner surface of the first flexible packaging layer, said second electronic component spaced apart from said first electronic component;
a contact via layer having a second flexible packaging layer positioned over the inner surface of said electronics layer, said contact via layer having a first contact via extending through the second flexible packaging layer and aligned with the first conductive contact, and a second contact via extending through the second flexible packaging layer and aligned with the second conductive contact, wherein said second flexible packaging layer is bendable and stretchable;
an interconnect layer having a third flexible packaging layer positioned over said contact via layer, said interconnect layer having an interconnect channel with a first end aligned with and in flow communication with the first contact via and a second end aligned with and in flow communication with the second contact via, wherein said third flexible packaging layer is bendable and stretchable;
a conductive material in said first contact via, second contact via and interconnect channel to electrically couple the first conductive contact of the first electronic component with the second conductive contact of the second electronic component; and
at least one connector having a locking position to lock the sensor in a ring shape, and an unlocked position whereby the sensor has a substantially linear shape that is configured to attach by gel to and conform with a body of a patient as a wearable patch,
wherein touching the ECG sensor to different locations on the body of the patient at different times provides asynchronous multi-lead ECG measurements.

14. The sensor of claim 13, wherein said first electronic component comprises an electrode and said second electronic component comprises a processing device.

15. The sensor of claim 14, wherein said electrode is spaced apart from the first conductive contact, and further comprising a wire connecting said electrode to the first conductive contact.

16. The sensor of claim 13, said interconnect layer further comprising an injection via extending through the third packaging layer, said injection via connected to and in flow communication with the interconnect channel, whereby the conductive material can be introduced into the interconnect channel, first contact via, and second contact via through the injection via.

17. The sensor of claim 16, further comprising a flexible seal on the interconnect layer over the injection via to seal the conductive material in the sensor, wherein said flexible seal is bendable and stretchable.

18. The sensor of claim 13, said first electronic component comprising an electrode embedded in the first packaging layer and exposed at an outer surface opposite the inner surface.

19. The sensor of claim 13, wherein the contact via layer has a first surface and a second surface, the first surface in direct contact with the inner surface of said electronics layer, and the interconnect layer is in direct contact with the second surface of the contact via layer.

20. The sensor of claim 19, wherein the electronics layer, contact via layer and interconnect layer are thin and elongated, and the first surface, second surface, and inner surface are continuous.

21. The sensor of claim 13, further comprising multiple ECG sensors; wherein touching the multiple ECG sensors to different locations on the body of the patient at the same time provides simultaneous multi-lead ECG measurements.

22. A method of forming an electrocardiogram (ECG) sensor, the method comprising:
forming an electronics layer having a first flexible packaging layer with an inner surface, wherein said first flexible packaging layer is bendable and stretchable;
embedding a first electronic component having a first conductive contact in the first flexible packaging layer with at least a portion of the first conductive contact exposed at the inner surface of the first flexible packaging layer;
embedding a second electronic component having a second conductive contact in the first flexible packaging layer with at least a portion of the second conductive contact exposed at the inner surface of the first flexible packaging layer, wherein the second electronic component is spaced apart from said first electronic component;
forming a contact via layer having a second flexible packaging layer having a first contact via and a second contact via, the first and second contact vias extending through the second flexible packaging layer, wherein said second flexible packaging layer is bendable and stretchable;
placing the contact via layer over the inner surface of the electronics layer, wherein the first contact via is aligned with the first conductive contact, and the second contact via is aligned with the second conductive contact;
forming an interconnect layer having a third flexible packaging layer, wherein the interconnect layer has an elongated interconnect channel with a first end and a second end, wherein said third flexible packaging layer is bendable and stretchable;
placing the interconnect layer over the contact via layer with the first end of the interconnect channel aligned with and in flow communication with the first contact via and the second end of the interconnect channel aligned with and in flow communication with the second contact via;
introducing a conductive material in the first contact via, second contact via and interconnect channel to electrically couple the first conductive contact of the first electronic component with the second conductive contact of the second electronic component;
wherein the sensor has a locking position that locks the sensor in a ring shape, and an unlocked position whereby the sensor has a substantially linear shape that is configured to attach by gel to and conform with the a body of the a patient as a wearable patch, and touching the ECG sensor to different locations on the body of the patient at different times to provide asynchronous multi-lead ECG measurements.

23. The method of claim 22, further comprising having multiple ECG sensors; wherein touching the multiple ECG sensors to different locations on the body of the patient at the same time provides simultaneous multi-lead ECG measurements.

24. An electrocardiogram (ECG) sensor comprising:
a flexible thin ring-shaped substrate configured to be worn about a finger of a patient, said substrate having an inner surface and an outer surface opposite the inner surface, wherein said substrate is bendable and stretchable;
a first ECG electrode positioned at the outer surface of said substrate;
a second ECG electrode positioned at the inner surface of said substrate configured to be in contact with the finger of the patient, whereby the first and second ECG electrodes receive a single-lead ECG signal when the first ECG electrode is touched to a body of the patient;
at least one connector having a locking position to lock the sensor in a ring shape, and an unlocked position whereby the sensor has a substantially linear shape that is configured to attach by gel to and conform with the body of the patient as a wearable patch,
wherein wearing multiple ECG sensors and touching the first ECG electrode of each of the multiple ECG sensors to different locations on the body of the patient at the same time provides simultaneous multi-lead ECG measurements.

25. The sensor of claim 23, further comprising a sensor processing device configured in the ECG sensor with said first and second ECG electrodes to receive the ECG signal from the first and second ECG electrodes; and further comprising a liquid conductive material embedded in said substrate to electrically couple said sensor processing device with said first ECG electrode and with said second ECG electrode.

* * * * *